United States Patent [19]

Frazier

[11] Patent Number: 5,876,582
[45] Date of Patent: Mar. 2, 1999

[54] METHODS FOR PREPARING DEVICES HAVING METALLIC HOLLOW MICROCHANNELS ON PLANAR SUBSTRATE SURFACES

[75] Inventor: A. Bruno Frazier, Salt Lake City, Utah

[73] Assignee: The University of Utah Research Foundation, Salt Lake City, Utah

[21] Appl. No.: 928,988

[22] Filed: Sep. 12, 1997

Related U.S. Application Data

[62] Division of Ser. No. 789,013, Jan. 27, 1997.
[51] Int. Cl.$^6$ .............................. C25D 1/02; C25D 5/02
[52] U.S. Cl. .............................. 205/122; 205/73; 205/75; 205/127
[58] Field of Search .................... 205/67, 73, 75, 205/118, 122, 127, 128, 145, 150, 151

[56] References Cited

U.S. PATENT DOCUMENTS

| | | | |
|---|---|---|---|
| 4,285,779 | 8/1981 | Shiga et al. | 205/73 |
| 4,530,740 | 7/1985 | Wolf et al. | 205/73 |
| 4,707,225 | 11/1987 | Schuler et al. | 205/73 |
| 4,871,623 | 10/1989 | Hoopman et al. | 428/586 |
| 4,894,664 | 1/1990 | Pah | 347/63 |
| 4,972,204 | 11/1990 | Sexton | 347/47 |
| 5,199,487 | 4/1993 | DiFrancesco et al. | 165/168 |
| 5,311,896 | 5/1994 | Kaartinen | 137/15 |

*Primary Examiner*—Kathryn Gorgos
*Assistant Examiner*—William T. Leader
*Attorney, Agent, or Firm*—Workman, Nydegger & Seeley; Gregory M. Taylor

[57] ABSTRACT

The present invention is directed to methods for preparing devices having hollow metallic microchannels on a surface of a planar substrate. More specifically, the present invention is directed to methods for preparing devices having surface metallic microchannels with a range of widths and heights selected to provide efficient flow characteristics and having thick and, thus, strong and durable channel walls. In addition, the methods of the present invention are compatible with standard integrated circuit fabrication techniques and, because the microchannels are formed upon the surface of the substrate without degrading the surface planarity, these techniques can be used to incorporate electronic circuitry into the microchannel-containing devices. For purposes of this application, the term "microchannel" refers to enclosed or partially enclosed channels having heights within the range from about 2 to about 200 micrometers ($\mu$m) and widths within the range of about 10 micrometers to about 2 millimeters.

5 Claims, 2 Drawing Sheets

METHODS FOR PREPARING DEVICES HAVING METALLIC HOLLOW MICROCHANNELS ON PLANAR SUBSTRATE SURFACES

This application is a divisional of application Ser. No. 08/789,013, filed Jan. 27, 1997, pending.

BACKGROUND OF THE INVENTION

1. The Field of the Invention

The present invention is directed to methods for preparing devices having hollow microchannels for use in various applications.

2. The Relevant Technology

Microchannel-containing devices have applications in various fields ranging from medical instrumentation to basic research in life sciences, earth sciences, and engineering. Hollow microchannels permit controlled dispensing of very small, i.e., microscale, quantities of fluid, such as, for example, in ink jet printers, or for virtually any type of preparation and/or analysis processing of microscale sample quantities. For purposes of this application, the term "microchannel" refers to enclosed or partially enclosed channels having heights within the range from about 2 to about 200 micrometers ($\mu$m) and widths within the range of about 5 micrometers to about 2 millimeters. Exemplary micro analysis systems developed within the biotechnology field include gas chromatography, liquid chromatography, free-flow fractionation, electrophoresis, and polymerase chain reaction which require miniaturized channels for reactant delivery and biochemical reaction chambers.

Presently known techniques for fabricating hollow microchannels include etching or machining methods which form channels in the substrate surface. For example, narrow channels may be etched, by various known methods, into the surface of a substrate such as silicon, glass, or quartz and a cover plate, typically made of glass, is then bonded to the substrate surface such that the cover plate forms one side of the etched microchannels. These microchannels are typically up to about 50 micrometers in depth. Alternatively, narrow channel "halves" may be machined into two plastic substrates which are then aligned with each other and bonded together such that hollow microchannels are formed between the two bonded plastic substrates. This method can form hollow microchannels having circular profiles and diameters within the range of about 0.5 mm to about 1.6 mm.

For many microchannel applications, the addition of electronic circuitry connected to the microchannels or to the microchannel-containing device for various purposes is desirable. Electrodes can be used to resistively heat fluids inside hollow microchannels for processes, e.g., many biochemical reactions such as polymerase chain reactions, which require elevated temperatures. Electrical currents can also be used to effect field flows resulting in desired movement of fluids, or specific portions or components of fluids, within the microchannels, e.g., as in Electrical Field-Flow Fractionation separation systems for effecting biological cell separations based on molecular size differences. Signal processing circuitry is also valuable in many systems. Thus, it will be appreciated that it is often desirable to be able to incorporate integrated circuits into a microchannel-containing device.

The above-described methods suffer from the drawback of being incompatible with standard integrated circuit fabrication techniques. Because the planarity of the substrate surface is disrupted by the channel etching or machining process, neither of the above-described methods are compatible with a subsequent integrated circuit fabrication process. Thus, these microchannel forming methods are not compatible with subsequent incorporation of integrated circuitry.

There are some methods of forming hollow microchannels close to, or on, the surface of planar substrates such that electrodes or sensors may be subsequently integrated. One such method involves undercutting an etch mask during a wet etching process on a silicon or quartz substrate. The resulting partially closed channel is sealed with a silicon nitride or other suitable material deposited by a low pressure chemical vapor deposition (LPCVD) process. The depth of these channels may range from about 20 to about 100 micrometers. Another method uses a suitable deposition process, such as LPCVD, to deposit sacrificial phosphosilicate-glass (PSG) material upon a substrate surface to define the inner dimensions of a hollow microchannel being formed. A silicon nitride, silicon dioxide, or other suitable dielectric is deposited by LPCVD or other deposition process over the PSG, which is then removed using hydrofluoric acid. These microchannels are typically about 1–2 micrometers in both width and height.

While the just described methods of forming microchannels are compatible with subsequent integrated circuit fabrication, these methods have other drawbacks. The LPCVD process requires elevated temperatures which may be detrimental to other materials desired to be used in the microchannel-containing device. In addition, at least one wall of the hollow microchannel is formed by the deposited dielectric material. It is not possible to form this material into a relatively thick or a wide wall. Thus, the inner width and inner height of the hollow microchannel itself, as well as the thickness of the microchannel wall(s), is limited by these material limitations. The limited channel width and height results in problems in the flow dynamics of the microchannel since more pressure is required to move fluid through a narrower, rather than a wider, channel. The limited wall thickness decreases the strength and durability of the microchannel in general and is particularly a problem in view of the potentially high fluid pressures due to the limited widths and heights of the channels.

None of the above-described methods provide hollow metal microchannels. Metal microchannels have advantages over other materials for many applications. For example, metal or metal coated microchannels exhibit excellent strength and durability and certain metals are compatible with many process conditions including biochemical reactions. Currently, there is no method available for preparing hollow metallic microchannels on the surface of planar substrates.

In view of the above, it would be an advance in the art to provide methods of preparing devices having hollow metallic microchannels on a surface of a planar substrate. It would be a further advance to provide methods of preparing devices having surface metallic microchannels which do not require elevated temperatures and are compatible with standard integrated circuit fabrication techniques. In addition, methods of preparing devices having durable, thick-walled surface metallic microchannels with relatively large cross sections that provide efficient flow characteristics would be an advancement in the art.

SUMMARY AND OBJECTS OF THE INVENTION

It is an object of the present invention to provide methods for preparing devices having hollow metallic microchannels on the surface of a planar substrate.

It is another object of the present invention to provide low temperature methods for preparing devices having surface metallic microchannels which are compatible with standard integrated circuit fabrication techniques.

It is a further object of the present invention to provide methods for preparing devices having surface metallic microchannels with thick walls.

Yet another object of the present invention is to provide methods for preparing devices having surface metallic microchannels with relatively large cross sections that provide efficient flow characteristics.

These and other objects and features of the present invention will become more fully apparent from the following description and appended claims, or may be learned by the practice of the invention as set forth hereinafter.

The present invention is directed to methods for preparing devices having hollow metallic microchannels on a surface of a planar substrate. More specifically, the present invention is directed to methods for preparing devices having surface metallic microchannels with a range of widths and heights selected to provide efficient flow characteristics and having thick and, thus, strong and durable channel walls. In addition, the methods of the present invention are compatible with standard integrated circuit fabrication techniques and, because the microchannels are formed upon the surface of the substrate without degrading the surface planarity, these techniques can be used to incorporate electronic circuitry into the microchannel-containing devices.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Microchannel-containing devices have applications in various fields ranging from medical instrumentation to basic research in life sciences, earth sciences, and engineering. Hollow microchannels permit controlled dispensing of very small, i.e., microscale, quantities of fluid, such as, for example, in ink jet printers, or for virtually any type of preparation and/or analysis processing of microscale sample quantities. For purposes of this application, the term "microchannel" refers to enclosed or partially enclosed channels having heights within the range from about 2 to about 200 micrometers ($\mu$m) and widths within the range of about 5 micrometers to about 2 millimeters. Exemplary micro analysis systems developed within the biotechnology field include gas chromatography, liquid chromatography, free-flow fractionation, electrophoresis, and polymerase chain reaction which require miniaturized channels for reactant delivery and biochemical reaction chambers.

Metal microchannels have advantages over other materials for some applications. For example, metal or metal coated microchannels exhibit excellent strength and durability and are compatible with many process conditions including biochemical reactions. Currently, there is no method available for preparing hollow metallic microchannels on the surface of planar substrates.

The present invention is directed to methods for preparing devices having hollow metallic microchannels on a surface of a planar substrate without degrading the surface planarity. The methods of the present invention do not employ high temperatures which can be detrimental to some materials desired to be used in microchannel construction. The methods of the present invention are compatible with standard integrated circuit fabrication techniques such that, following microchannel fabrication, these techniques can be used to incorporate electronic circuitry into the same substrate.

The wall thickness of the microchannels of the present invention can be selectively controlled to ensure that the microchannel walls are strong and durable. In addition, unlike conventional micro channels, the present invention provides methods for preparing devices having surface metallic microchannels with a range of widths and heights selected to provide efficient flow characteristics. In particular, the hollow microchannels of the present invention can be formed to have wide rectangular cross sections wherein the inner height of the channel is significantly less than the inner width of the channel. As seen in Table 1, which shows the pressures required to sustain laminar flow of DI water (Newtonian fluid) through microchannels of various dimensions at a flow rate of 0.5 $\mu$L/s, doubling the width of the microchannels roughly halved the required pressure. Thus, it is advantageous to be able to prepare hollow microchannels having large cross sections.

TABLE 1

Pressures Required to Move DI Water at 0.5 $\mu$L/s Through 10 mm Long Microchannels

| Width ($\mu$m) | Height ($\mu$m) | Pressure (kPa) |
| --- | --- | --- |
| 100 | 50 | 3.5 |
| 100 | 25 | 25.5 |
| 100 | 15 | 119.2 |
| 200 | 50 | 1.6 |
| 200 | 25 | 12.9 |
| 200 | 15 | 60.2 |

EXAMPLES

The following hollow metallic microchannels have been fabricated using common clean room techniques and equipment. In each case, all of the listed metal types have been fabricated on each of the listed substrates using the same fabrication procedure.

Metal types

Nickel (using a Watts electrolytic solution)
Nickel (using a nickel sulfamate electrolytic solution)
Copper (using a cupric sulfate acid electrolytic solution)
Gold (using a gold cyanide electrolytic solution)
Substrates
Silicon
Standard Glass
Pyrex 7740
Alumina Ceramic

| Microchannel Dimensions | | | |
|---|---|---|---|
| Length | Inner Width | Inner Height | Wall Thickness |
| 16 mm | 1.5 mm | 30 $\mu$m, 50 $\mu$m | 30 $\mu$m |
| 16 mm | 0.6 mm, 1.5 mm | 30 $\mu$m, 50 $\mu$m | 30 $\mu$m |
| 3.35 mm | 0.4 mm, 0.1 mm | 5 $\mu$m, 20 $\mu$m | 10 $\mu$m, 20 $\mu$m |
| 9.75 mm | 0.4 mm, 0.6 mm | 20 $\mu$m, 100 $\mu$m | 2 $\mu$m, 100 $\mu$m |
| 7.625 mm | 0.4 mm, 0.6 mm | 5 $\mu$m, 50 $\mu$m | 2 $\mu$m, 50 $\mu$m |
| 10.25 mm | 1.0 mm, 0.4 mm | 10 $\mu$m, 150 $\mu$m | 5 $\mu$m, 100 $\mu$m |

Figure 1:
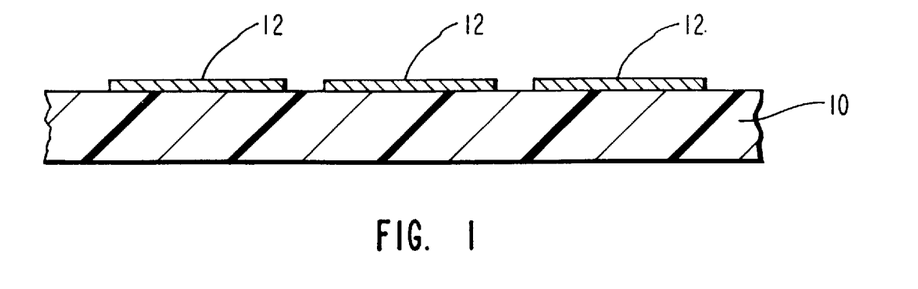
FIG. 1 is a cross-section view of a device being prepared in accord with the present invention.
Figure 2:
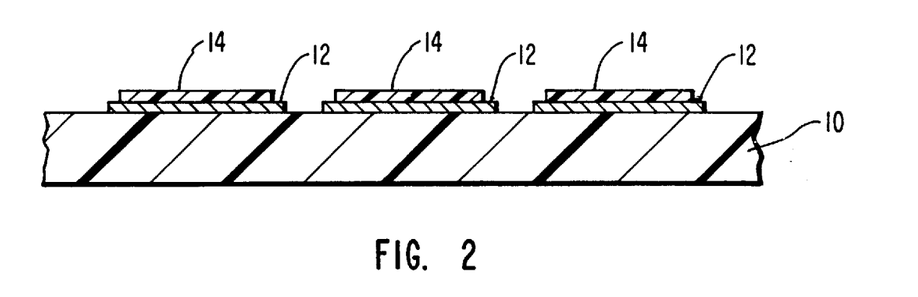
FIG. 2 is a cross-section view of a device being prepared in accord with the present invention.
Figure 3:
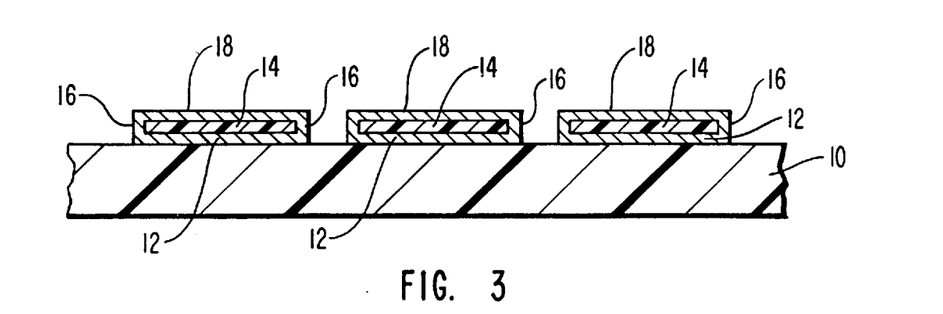
FIG. 3 is a cross-section view of a device being prepared in accord with the present invention.
Figure 4:
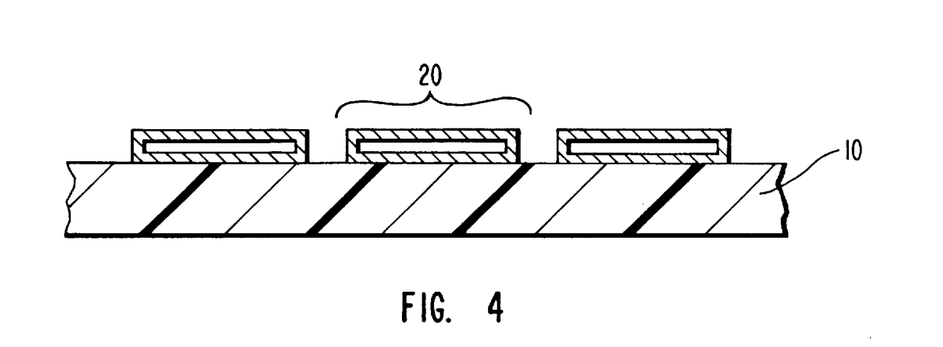
FIG. 4 is a cross-section view of a device prepared in accord with the present invention.

Fabrication Procedure:
1. Clean the substrate.
2. Physical vapor deposit an adhesion layer (titanium, 100 Angstroms) upon the entire substrate surface. Electron beam evaporation with a Denton. Vacuum E-beam Evaporator was used, however, other low temperature coating deposition methods could be used. The adhesion layer can be any suitable adhesion material such as chromium or titanium and the thickness of this layer can be within the range of about 100 to about 2000 Angstroms.
3. Physical vapor deposit an electroplating seed layer (100 Angstroms) over the entire substrate surface. (In this case, the substrate surface is coated with the adhesion layer material. As used herein, reference to a "surface" or a "substrate surface" may refer to either a coated or uncoated surface.) Electron beam evaporation with a Denton Vacuum E-beam Evaporator was used. The seed layer can be any suitable metal, e.g., copper or gold in a thickness range of about 100 to about 2000 Angstroms.
4. Physical vapor deposit a second adhesion layer (chromium, 1000 Angstroms) upon the entire substrate surface. Electron beam evaporation with a Denton Vacuum E-beam Evaporator was used. Again, the adhesion layer can be any suitable adhesion material such as chromium or titanium and the thickness of this layer can be within the range of about 100 to about 2000 Angstroms.
5. Spin coat (or other suitable coating method) and pattern a first micro molding layer comprising a positive photoresist material for defining the selected location of the microchannel bottom walls.
6. Remove the second adhesion layer in the areas not masked by the first photoresist layer and expose the underlying seed layer.
7. Electroplate the bottom wall of the microchannels with the selected metal to the selected wall thickness. Suitable metals include gold, silver, nickel, copper and combinations of these. FIG. 1 is a cross-section view of a substrate 10 having bottom walls 12 formed thereon.
8. Remove the first photoresist layer (using consecutive applications of acetone, methanol, and water).
9. Remove the exposed second adhesion layer, seed layer, and first adhesion layer consecutively using wet etching. (Note that the portion of these layers which are beneath the electroplated bottom wall are not exposed and, thus, are not removed.)
10. Spin coat (or other suitable coating method) and pattern a second positive photoresist layer on top of the electro- formed bottom walls. The thickness of this layer defines the inner height of the microchannel. FIG. 2 illustrates the photoresist layer 14 patterned on the bottom walls 12 formed upon the substrate 10 as shown in FIG. 1.
11. Deposit a third adhesion layer over the substrate surface and the bottom walls coated with photoresist. Sputter deposition is preferred to ensure good coverage of the sides of the thick photoresist layers. A Denton Vacuum Model 15 was used and the adhesion material was 100 Angstroms of titanium.
12. Deposit a second electroplating seed layer over the third adhesion layer. Again, sputter deposition is preferred and was accomplished with the Denton Vacuum Model 15. The material was either copper or gold in a layer 1000 Angstroms thick.
13. Spin coat (or other suitable coating method) and pattern a third positive photoresist layer on top of the second seed layer. The pattern is such that all areas are masked except for the areas where the bottom walls and thick photoresist layers are located.
14. Electroplate the exposed second seed layer where the bottom walls and thick photoresist layers are located to form top and side walls of the microchannels with the selected metal to the selected wall thickness. FIG. 3 illustrates the side walls 16 and top walls 18 electroformed on the on the bottom walls 12.
15. Remove the third and second photoresist layers using consecutive applications of acetone, methanol, and water. This steps forms the hollow microchannel. (It has been surprisingly discovered that the times associated with the release of the thick photoresist layer from within the microchannels increase with larger microchannel cross-sections. For example, a 1 mm wide, 30 $\mu$m high, and 7 mm long microchannel on a glass substrate took approximately 5 hours to release while a 100×30×500 $\mu$m (W×H× L) channel took less than 2 hours.)
16. Remove the second seed layer and third adhesion layer using a suitable process such as reverse sputtering or wet etching. FIG. 4 depicts the hollow microchannels 20 formed on the surface of the substrate 10.

Figure 5:
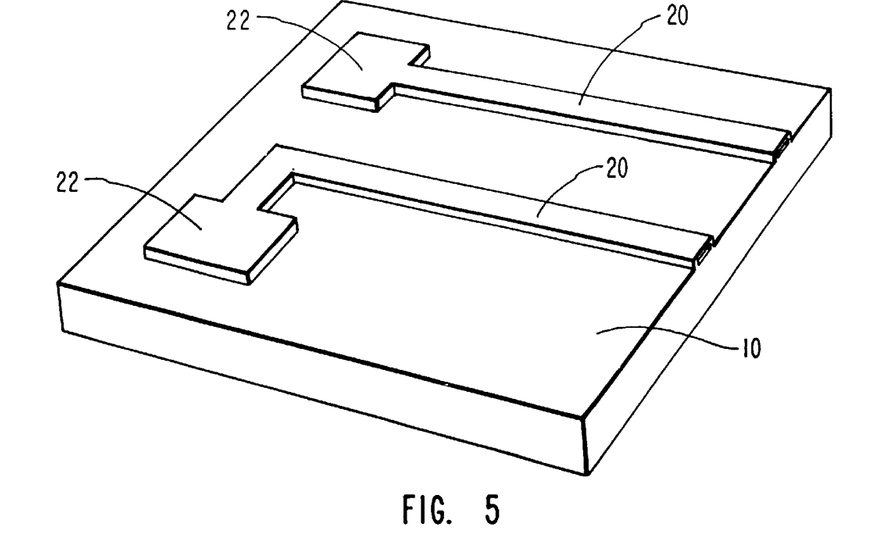
FIG. 5 is a perspective view of a device in accord with the present invention.

FIG. 5 is a perspective view of the top of a substrate 10 having hollow metallic microchannels 20 formed on its surface in accord with the present invention. It will be appreciated that the metallic microchannel walls, and particularly the inside walls of the microchannels, could be coated with many types of materials using low temperature deposition processes, if desired. As shown in FIG. 5, it may be desired to form closed reservoirs 22 at one end of the microchannels.

Figure 6:
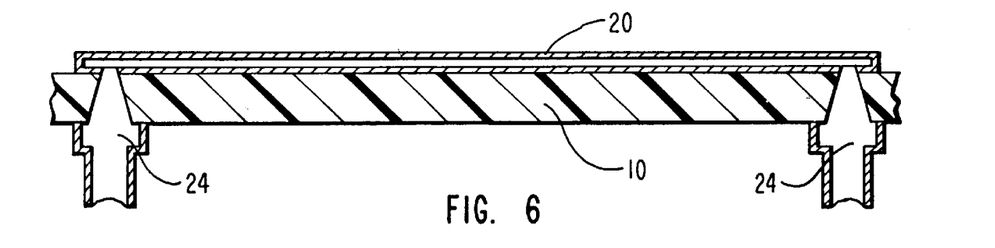
FIG. 6 is a longitudinal section view of a device in accord with the present invention.

Fluid transfer ports for inputting and outputting fluids through the microchannels may be made, for example, through the side walls or the top walls of the microchannel walls. Alternatively, if desired, such fluid transfer ports may be formed through the underlying substrate and the bottom wall of the microchannel. FIG. 6 depicts a longitudinal section of a hollow microchannel 20 on the surface of a substrate 10 which is accessible by two fluid transfer ports 24 etched through the substrate and the bottom wall of the microchannel. It will be appreciated that such ports could be used to allow milli-scale interface between microchannels and macrotubing and/or to effect pressure control through the microchannels. If desired, the ports could communicate with reservoir compartments on the opposite side of the substrate from the microchannels.

It will be appreciated that access into a reservoir formed at one end of one, or more, microchannels, could similarly be provided through a side wall or top wall or, through the underlying substrate and reservoir bottom wall. It will be further appreciated that the hollow microchannels can be interconnected in any desired manner. For example, interconnecting microchannels can be formed on the substrate surface or multiple microchannels could interconnect through a common reservoir. Similarly, fluid transfer ports etched through the substrate and bottom walls of multiple microchannels, as shown in FIG. 6, could be used to interconnect those microchannels. If desired, different fluids could be intermixed within the microchannels through input through separate ports communicating with a common reservoir or with multiple interconnected microchannels.

Figure 7:
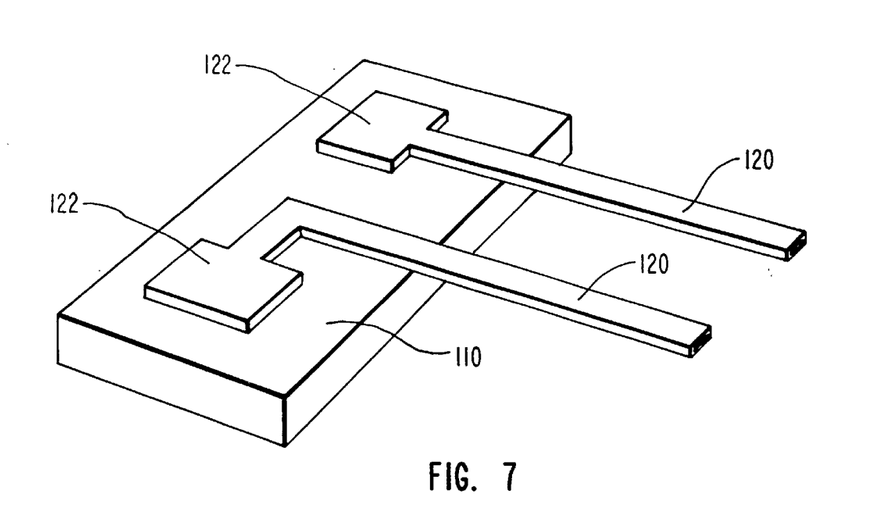
FIG. 7 is a perspective view of a device in accord with the present invention.

For some applications, it would be useful to extend, i.e., cantilever, hollow metallic microchannels from the end of the substrate as illustrated in FIG. 7. FIG. 7 depicts a substrate 110 having surface hollow microchannels 120 with closed reservoir ends 122 which are cantilevered and, thus, suspended beyond the substrate edge. These cantilevered microchannels are fabricated in the same manner as described above except that conventional sacrificial p+ boron doped membrane technology is used to, initially, prepare a portion of a silicon substrate as a sacrificial membrane and, following fabrication of the hollow metallic microchannels, to remove the sacrificial membrane from beneath that portion of the microchannels formed thereon by an etching process. In this manner, a portion of the microchannels is cantilevered from the substrate.

It will be appreciated that standard integrated circuit technology could be used to form integrated circuitry upon the surface of the substrate and/or upon the hollow microchannels. It will be further appreciated that microchannels prepared in accord with the present invention could be formed on multiple levels upon a substrate surface. The different levels of microchannels could be formed to cross over and under each other and to interconnect through fluid transfer ports and/or common reservoirs as described above for single level microchannels.

Micropipette Arrays

An exemplary application for the devices of the present invention would be as micropipette arrays which could be used for various microscale sample preparation and/or analysis systems and also for interfacing conventional macro instrumentation to micro instrumentation. An advantage of the devices of the present invention is that the precise control of the inner channel dimensions permits precise measurement and control of fluid volumes to be dispensed, sampled, prepared, and/or analyzed. For example, sample volumes within the range of about 25 picoliters to about 10 microliters can be readily assayed with micropipettes made in accord with the present invention. Another advantage is the low cost and efficient batch fabricating techniques can be utilized to prepare devices in accord with the present invention such that hollow microchannels can be fabricated in arrays comprising hundreds of microchannels formed on the surface of suitably sized substrates. Such arrays would be useful for applications facilitated by parallel processing capabilities, e.g., DNA sequencing systems.

The configuration of the arrayed microchannels can be customized for a given application. For example, the center-to-center spacing of the microchannels can range from about 40 millimeters down to about 40 micrometers. The microchannel arrays can also be customized for interfacing with macro scale systems and instrumentation. For example, connecting channels could be formed through the substrate and through the bottom wall of the microchannel which are suitably sized for macro channel interfacing at the substrate surface. In addition, because a variety of metals and insulator materials, or combinations thereof, can be utilized in accord with the present invention, the devices can be adapted for multiple function application such as rapid polymerase chain reaction processes and in-line separations of cellular sample components.

Microchannel Ink Jet Nozzles

Another exemplary application for the devices of the present invention would be as ink jet nozzles. Recently developed laser printer systems utilize arrays of micromachined ink jet nozzles as the means of achieving high resolution and high speed printing. During operation of the printers, select micro nozzles in the array(s) are addressed in order to produce a series of high resolution dots. The ultimate resolution of the printer system is given in dots per inch and is determined (at least to the first order) by nozzle spacing, nozzle diameter, and the jet profile characteristics. The maximum speed of a given print operation is determined by the rate of data conversion and the actuation speed of the micro nozzles.

Two important design and marketing parameters for printer systems are the resolution and the speed of the printer. Microchannel arrays in accord with the present invention could be utilized to significantly increase the resolution and speed of the ink jet dispensing operation. The ink could be distributed to individual microchannels via a central feed attached to the opposite surface of the substrate and connected to the microchannels by a port through the substrate and the bottom wall of the microchannels. Using a cantilevered arrays of the microchannels, the ink jet streams could be produced to form dots and continuous lines. Dots can be produced by actuation of the channels, e.g., by thermal actuation. Lines can be produced by a combination of actuation and mechanical movement of the extending portions of the microchannels. Mechanical movement can be achieved using several approaches including electromagnetic actuation or thermal actuation of a bimorph structure. Two dimensional and/or stacked three dimensional arrays of the microchannels can be used to form a print head.

Advantages include increased print resolution by printing line segments instead of individual dots, increased speed by replacing multiple micro nozzles with a single microchannel for printing line segments, and increased system speed by decreasing the number of elements to be addressed to produce line segments and by decreasing the size of the converted data file.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for preparing hollow metallic microchannels on a substrate surface, said method comprising the steps of:
  a) depositing a first electroplating seed layer over a substrate surface;
  b) selectively electroplating said first electroplating seed layer with a selected metal to thereby form each metallic bottom wall of a microchannel;
  c) selectively coating a top surface of each said metallic bottom wall with a photoresist layer to a height corresponding to a selected inner height of each microchannel;
  d) depositing a second electroplating seed layer over said substrate having metallic bottom walls thereon;

e) selectively electroplating said second electroplating seed layer with a selected metal to thereby form side walls and a top wall upon each bottom wall and surrounding said photoresist layer, said electroplating continuing until a desired thickness for said side walls and top walls is achieved; and f) removing said photoresist layer from between the walls of each microchannel to thereby hollow the microchannel.

2. A method for preparing cantilevered hollow metallic microchannels on a silicon substrate, said method comprising the steps of:

a) forming a sacrificial membrane comprising p+ boron in a portion of a silicon substrate;

b) depositing a first electroplating seed layer over a surface of said substrate having a sacrificial membrane portion;

c) selectively electroplating said first electroplating seed layer with a selected metal to thereby form each metallic bottom wall of a microchannel;

d) selectively coating a top surface of each said metallic bottom wall with a photoresist layer to a height corresponding to a selected inner height of each microchannel;

e) depositing a second electroplating seed layer over said substrate having metallic bottom walls thereon;

f) selectively electroplating said second electroplating seed layer with a selected metal to thereby form side walls and a top wall upon each bottom wall and surrounding said photoresist layer, said electroplating continuing until a desired thickness for said side walls and top walls is achieved;

g) removing said photoresist layer from between the walls of each microchannel to thereby hollow each said microchannel; and h) removing said sacrificial membrane portion to thereby cantilever the portion of said metallic microchannels formed upon said sacrificial membrane portion of said silicon substrate.

3. A method for preparing hollow metallic microchannels on a substrate surface, said method comprising the steps of:

a) depositing a first adhesion layer over a surface of a substrate;

b) depositing a first electroplating seed layer over said first adhesion layer;

c) depositing a second adhesion layer over said first electroplating seed layer;

d) selectively coating said second adhesion layer with a first photoresist layer;

e) removing portions of said second adhesion layer not coated by said first photoresist layer to thereby expose underlying portions of said first electroplating seed layer, each exposed portion of said first electroplating seed layer defining a location of a bottom wall of a microchannel;

f) electroplating said exposed portions of said first electroplating seed layer with a selected metal to thereby form each metallic bottom wall of a microchannel;

g) removing said first photoresist layer and portions of said second adhesion layer, said first electroplating seed layer, and said first adhesion layer underlying said first photoresist layer;

h) selectively coating a top surface of each said metallic bottom wall with a second photoresist layer to height corresponding to a selected inner height of each microchannel;

i) depositing a third adhesion layer over said substrate surface and said metallic bottom walls coated with said second photoresist layer coating thereon;

j) depositing a second electroplating seed layer upon said third adhesion layer;

k) selectively coating portions of said second electroplating seed layer with a third photoresist layer such that uncoated portions of said second electroplating seed layer define the locations of the underlying metallic bottom walls;

l) electroplating said uncoated portions of said second electroplating seed layer with a selected metal to thereby form side walls and a top wall upon each bottom wall, said electroplating continuing until a desired thickness for said side walls and top walls is achieved; and m) removing said third photoresist layer and underlying portions of said second electroplating seed layer, said third adhesion layer, and said second photoresist layer to thereby hollow each said microchannel.

4. A method for preparing hollow metallic microchannels on a substrate surface as described in claim 3 further comprising the step of forming an access channel to a microchannel, said access channel being formed through the substrate and through the bottom wall of said microchannel.

5. A method for preparing hollow metallic microchannels on a substrate surface as described in claim 3 further comprising the step of forming a reservoir at one end of a microchannel, said reservoir comprising a portion of said bottom wall, side walls, and top wall of said microchannel and having an end wall perpendicular to each of said bottom wall, side walls, and top wall.

* * * * *

UNITED STATES PATENT AND TRADEMARK OFFICE
CERTIFICATE OF CORRECTION

PATENT NO. : 5,876,582
DATED : Mar. 2, 1999
INVENTOR(S) : A. Bruno Frazier

It is certified that error appears in the above-identified patent and that said Letters Patent are hereby corrected as shown below:

Cover Page, References Cited, left column, line 5, change "Pah" to --Pan--

Cover Page, right column, insert the following:

OTHER PUBLICATIONS

Frazier, A. Bruno; O'Brien, David P.; and Allen, Mark G., *"Two Dimensional Metallic Microelectrode Arrays for Extracellular Stimulation and Recording of Neurons,"* MicroElectro Mechanical System Conference, Ft. Lauderdale, Florida, January, 1993.

Col. 5, line 24, after "Denton" delete the period

Signed and Sealed this

Fourteenth Day of December, 1999

Attest:

Q. TODD DICKINSON

*Attesting Officer*

*Acting Commissioner of Patents and Trademarks*

UNITED STATES PATENT AND TRADEMARK OFFICE
Certificate

Patent No. 5,876,582                                                         Patented: March 2, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of the patent is: A. Bruno Frazier and Ian Papasutsky.

Signed and Sealed this Sixth Day of March, 2001.

KATHRYN GORGOS
*Superviosry Patent Examiner*
Art Unit 1741

UNITED STATES PATENT AND TRADEMARK OFFICE
Certificate

Patent No. 5,876,582                  Patented: March 2, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: A. Bruno Frazier and Ian Papautsky.

Signed and Sealed this Eighth Day of May, 2001.

KATHRYN GORGOS
*Supervisory Patent Examiner*
Art Unit 1741